United States Patent [19]

Levine

[11] Patent Number: 5,062,420

[45] Date of Patent: Nov. 5, 1991

[54] SEALED SWIVEL FOR RESPIRATORY APPARATUS

[76] Inventor: Walter Levine, 6948 North Keating, Lincolnwood, Ill. 60646

[21] Appl. No.: 584,253

[22] Filed: Sep. 18, 1990

[51] Int. Cl.$^5$ .................. A61M 16/00; A62B 7/00
[52] U.S. Cl. .................. 128/204.18; 128/207.14; 128/912; 128/206.26; 128/205.25; 128/DIG. 26
[58] Field of Search .................. 128/200.24, 204.18, 128/205.25, 207.14, 911, 912; 285/168, 345

[56] References Cited

U.S. PATENT DOCUMENTS

| 3,556,097 | 1/1971 | Wallace | 128/202.23 |
|---|---|---|---|
| 3,707,972 | 1/1973 | Viliari | 128/912 |
| 4,249,527 | 2/1981 | Ko et al. | 128/911 |
| 4,254,773 | 3/1981 | Waldbillig | 128/247 |
| 4,416,273 | 11/1983 | Grimes . | |
| 4,469,835 | 9/1984 | Laurin | 128/912 |
| 4,612,929 | 9/1986 | Schübert et al. | 128/204.25 |
| 4,637,384 | 1/1987 | Schroeder | 128/204.18 |
| 4,676,241 | 6/1987 | Webb et al. . | |
| 4,790,832 | 12/1988 | Lopez | 128/912 |
| 4,794,921 | 1/1989 | Lindkvist | 128/203.29 |
| 4,827,921 | 5/1989 | Rugheimer | 128/912 |
| 4,938,209 | 7/1990 | Fry . | |
| 4,953,547 | 9/1990 | Poole Jr. | 128/203.12 |

Primary Examiner—Edgar S. Burr
Assistant Examiner—Lisa E. Malvaso
Attorney, Agent, or Firm—Welsh & Katz

[57] ABSTRACT

A sealed swivel for a respiratory apparatus includes a first end configured for engagement with either an endotracheal tube or a face mask, a second end with a telescoping formation for insertion into a tubular respiratory connector, and a central portion with a sealing formation defining a swivel track and configured for creating a gas tight seal while permitting relatively free swivelling action.

20 Claims, 1 Drawing Sheet

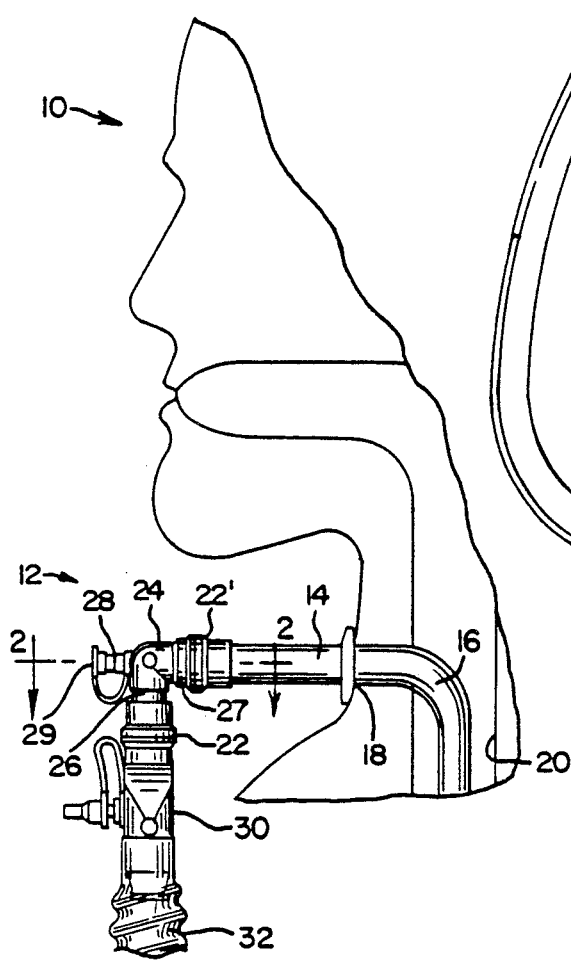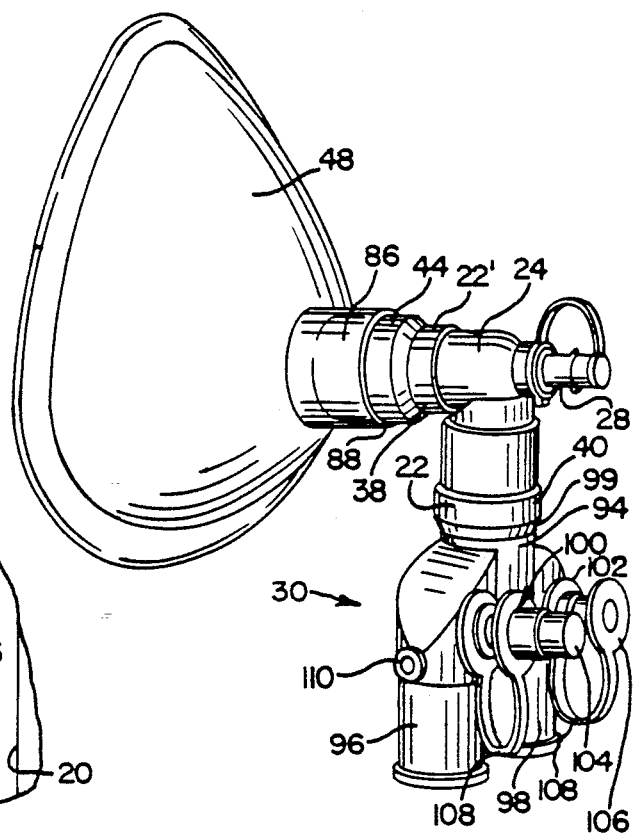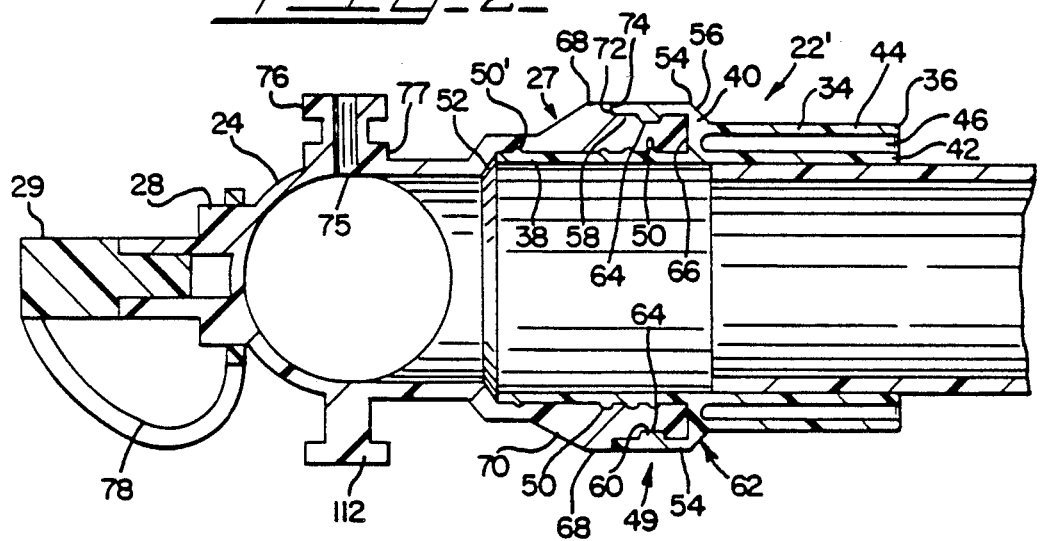

SEALED SWIVEL FOR RESPIRATORY APPARATUS

BACKGROUND OF THE INVENTION

The present invention relates generally to connecting systems for respiratory therapy apparatus, and specifically to such a connecting system designed to connect a first respiratory therapy device to a second device, the second device being secured to the patient.

During continuous mechanical ventilation/respiration of patients, a ventilation tube delivers air or oxygen to the patient from a remote source. The ventilation system often includes a 'Y'-piece having inhalation and exhalation sockets for connection to appropriate tubes, and a third socket for connection to the ventilation tube. The end of the ventilation tube is inserted into the patient's nostril (nasal endotracheal tube), into the patient's mouth (oral endotracheal tube), into a face mask releasably secured to the patient, or into an incision made in the patient's neck (endotracheal or tracheostomy tube) so that the tube may be inserted directly into the trachea. If the patient moves slightly, for example by moving his head, the tube may rub against sensitive surfaces inside the patient's respiratory tract, causing pain and/or injury.

Conventional respiratory connectors have addressed this problem by providing swivelling connectors between the 'Y'-piece and the patient. One disadvantage of such conventional connectors is that they are relatively easily dislodged from the ventilation tube and/or the patient connection, either by the patient or medical personnel. Since any disruption of the respiratory therapy may be fatal, or at a minimum, critical to the patient's condition, this disadvantage takes on added significance.

Another disadvantage of conventional connectors is that they form an ineffective seal which permits leakage of respiratory gases, often containing aerosolized medication or bacterial and/or viral particles. Aside from affecting the efficiency of treatment and the safety of the patient, this latter disadvantage may affect the health of attending physicians and/or health care workers.

Thus, there is a need for a swivelling connector for a respiratory therapy apparatus which is not easily disconnected from the ventilation tube and/or the patient, and which forms a gas-tight seal in the swivel area.

SUMMARY OF THE INVENTION

Accordingly, the swivelling respiratory connector of the invention addresses the above-identified disadvantages by providing a swivel member which may be securely and sealingly attached to at least one end of a tubular respiratory connector such as an elbow, while still providing relatively free swivelling action for optimum patient comfort.

More specifically, the sealed respiratory swivel member of the invention includes a tubular body having a first open end, a second open end and a central portion, the first open end having an inner diameter and an outer diameter, and the second end having a telescoping portion and formations for sealing the telescoping portion to a tubular member. The first open end may have a dual walled, dual diameter construction for engagement either with a respiratory face mask or an endotracheal tube. The telescoping portion in the second open end prevents disconnection of the swivel from the respective respiratory device or connector tube and has at least one annular sealing ring. The central portion includes a seal formation including an annular collar secured to the central portion by an annular shoulder in spaced, concentric relation, the collar having an inwardly projecting annular sealing rib. The swivel member is designed so that the second end may be inserted into a corresponding respiratory connector provided with a formation configured to sealingly engage both the second end and the central portion of the swivel member.

BRIEF DESCRIPTION OF THE DRAWING

FIG. 1 is an elevational view showing in diagrammatic form a patient with an endotracheal tube inserted through a tracheostomy opening in his neck, and illustrates a ventilation apparatus incorporating the swivelling respiratory connector of the invention;

FIG. 2 is a sectional view taken along the line 2—2 of FIG. 1 and in the line generally indicated; and FIG. 3 is a front perspective elevational view of the swivelling respiratory connector of the invention employed with a face mask.

DETAILED DESCRIPTION OF THE PREFERRED EMBODIMENT

Referring now to FIG. 1, a patient 10 is shown connected to a ventilating apparatus generally designated 12 such that oxygenated air can be introduced into the patient's lungs through a connector 14 which is connected to an endotracheal tube 16 provided in an opening 18 in the throat 20 of the patient 10. In regard to the present invention, the term "connected" will be understood to imply that the connected parts are in fluid communication with each other. The apparatus 12 causes the patient 10 to breathe normally as a result of the cyclical operation of the apparatus, which periodically introduces fresh air into the lungs and withdraws stale air according to conventional practice.

In conventional ventilation apparatus using rigid connectors, movement by the patient 10 during treatment may result in irritation, pain, and/or injury to the throat 20. In order to address this problem, the respiratory connector 14 includes at least one and preferably two swivel members 22 and 22' which are connected to a respiratory connector fitting shown as a tubular elbow fitting 24. It will be appreciated that the swivel member 22' and the swivel member 22 are identical except for their disposition upon the elbow fitting 24.

The elbow fitting 24 is preferably made of injection molded plastic, defines a 90 degree angle and includes first and second ends 26, 27 respectively, each of which is connected to a respective swivel member 22, 22'. The first end 26 may be designated the male end and is of generally straight tubular configuration. The second end 27 may be designated the female end and is of relatively more complicated construction, as will be described below.

The elbow 24 may also be provided with at least one access port 28 having a tethered cap 29. The access port 28 may be used to connect a suction line to the patient 10, or alternately, to connect a $CO_2$ sensor for selective or periodic monitoring of the mixture of respiratory gases. The swivel member 22 is also connected to a tubular 'Y'-piece 30 (best seen in FIG. 3) which may in turn be connected to a supply tube 32 for supplying oxygen, aerosolized medicine or other application materials.

Referring now to FIG. 2, the connection between the swivel member 22' and the female end 27 of the elbow fitting 24 is depicted in greater detail. The swivel member 22' has a generally tubular body 34 with a first open end 36, a second open end 38, also referred to as the telescoping end, and a central portion 40. The tubular body 34 is preferably made of polymeric plastic material, and may be injection molded.

The first open end 36 is preferably provided of dual wall construction to save material and to decrease the cycle time of the injection molding apparatus. The first end 36 is thus provided with an inner wall 42 and an outer wall 44 with a gap 46 defined therebetween. The inner wall 42 is dimensioned to matingly engage the endotracheal tube 16, and preferably has a diameter in the range of 12 to 17 mm. This diameter is also compatible with conventional oral, nasal endotracheal, and tracheostomy tubes. The outer wall 44 is dimensioned to matingly engage a face mask 48 (best seen in FIG. 3) and preferably has a diameter in the range of 19 to 25 mm.

A significant design factor addressed by the present swivel member 22 is the creation of a fluid tight seal at the swivel point, generally designated 49. Accordingly, the telescoping end 38 is provided with at least one and preferably several integral annular sealing bands 50. In the preferred embodiment, one such band, designated 50' is located adjacent an outer edge 52 of the telescoping end portion 38, and a group of three such bands 50 are located in spaced relationship to each other near the central portion 40.

In addition to the sealing bands 50, the sealed nature of each of the swivel members 22, 22' is provided in part by the central portion 40, which includes an annular collar 54 circumscribing the body 34 and being integrally secured thereto in spaced, concentric relation by an annular shoulder 56. The collar 54 has an inner surface 58 with an inwardly projecting annular sealing rib 60 centrally located thereon. The collar 54, the shoulder 56, and the rib 60 define a sealed swivel track 62 which is operationally engaged by the second or female end 27 of the elbow fitting 24.

The female end 27 of the elbow 24 operationally engages the track 62 and complements the central portion 40 of the swivel member 22. An annular groove 64 is located adjacent an outer edge 66 of the female end 27 and is dimensioned to slidingly and sealingly engage the sealing rib 60 on the collar 54. The female end 27 is also provided with a peripherally projecting annular ring 68 preferably having a shoulder 70. The ring 68 is configured to define a ledge 72 which slidingly engages an edge 74 of the collar 54. The relative positions of the groove 64 and the annular ring 68 are such that the groove is between the outer edge 66 and the ring.

Another design factor addressed by the present swivel member 22 is that it not be easily dislodged from the elbow fitting 24. In order to strengthen the connection between the swivel member 22 and the fitting 24, the second or telescoping end 38 is provided with a length which extends a substantial distance into the fitting 24. In the preferred embodiment, the length of the telescoping end 38 is on the order of 12 to 16 mm, or is such that the annular shoulder 56 of the collar 54 is generally equidistant from the edge 52 of the telescoping end and from an outer edge of the first end 36.

In addition to the access port 28, the elbow 24 may also be provided with a second port 75 (shown in FIG. 2 only) located in an offset position to the port 28 so as to not interfere with tubes inserted therethrough. The port 75, or for that matter, the port 28, may be configured as a luer fitting, which includes the provision of a segmented annular lug 76. The luer fitting is designed for the positive locking "push and twist" attachment of certain forms of conventional respiratory gas sensor fittings. An annular boss 77 may preferably be provided for the attachment of a tether strap 78 of a cap 29 as is shown provided for the access port 28.

Referring now to FIG. 3, the swivel member 22 is shown employed in conjunction with the face mask 48. The mask 48 is depicted as an emergency resuscitation mask, although it is contemplated that the present invention may be employed with any sort of therapeutic face mask, such as, but not limited to anesthesia and/or respiratory face masks. A nose formation 86 on the mask 48 has an access port 88 which is friction fit over the outer wall 44 of the first end 36 of the swivel member 22'. The swivel member 22' is then connected at its second end 38 to the elbow fitting 24. The male or first end 26 of the elbow is then inserted into the swivel 22 for swivelling connection with the 'Y'-piece 30 as shown and described previously in relation to FIG. 1.

The 'Y'-piece 30 is provided with a connector tube 94, an inhalation socket 96 and an exhalation socket 98. Both the inhalation and exhalation sockets, 96, 98 are in fluid communication with the connector tube 94. An upper end 99 of the connector tube 94 is provided with an identical configuration to the second or female end 27 of the elbow fitting 24 so as to sealingly and swivellingly accommodate the central portion 40 of the swivel member 22.

An access port 100, 102 is respectively provided in each of the inhalation and exhalation sockets, 96, 98 so that aerosol or vacuum lines may be attached to either socket or the 'Y'-piece 30 as a particular treatment may designate. The ports 100, 102 are each provided with a distinctive male or female configuration to prevent the inadvertent connection of the wrong line to a specific socket 96, 98. In the preferred embodiment, the port 100 in the inhalation socket 96 has a male configuration, being basically a tube projecting forwardly from the 'Y'-piece 30. The port 102 in the exhalation socket 98 has a female configuration, being basically a throughbore into the socket.

Each port 100, 102 also has a corresponding cover 104, 106, the covers being specifically designed for the particular port configuration. In the preferred embodiment, the same part may be used for both covers 104, 106, and is merely reversed 180° to suit the application. A tether strap 108 is provided to each cover 104, 106 and may be attached to the respective ports 100, 102 to prevent loss of the covers. In addition, at least one handling lug 110 may be integrally formed on the 'Y'-piece 30, and a similar lug 112 may be formed on the elbow fitting 24 (best seen in FIG. 2).

It is contemplated that the present swivel member 22 may be employed with any type of respiratory connector in which a sealing relationship is required, and wherein one end of such a connector may be configured to matingly engage one of the annular walls 42 or 44, or in the alternative, where the connector may be provided with an annular groove 64 and an annular ring 68 in the manner of the present elbow fitting 24 and the 'Y'-piece 30 for engaging the second open end 38 of the swivel member 22.

Thus, it will be seen that the present respiratory swivel provides an effective, gas tight sealed, swivelling action to respiratory connectors which is more securely held in, and more difficult to dislodge from, connecting fittings than conventionally available swivel connectors.

While a particular embodiment of the sealed respiratory swivel of the invention has been shown and described, it will be appreciated by those skilled in the art that changes and modifications may be made thereto without departing from the invention in its broader aspects and as set forth in the following claims.

What is claimed is:

1. A swivel member for a respiratory connector having a respiratory connector fitting, comprising:
   a tubular body having a first open end, a second open end and a central portion defining a swivel track adapted to sealingly and swivellingly engage an end of the connector fitting;
   said first open end having an inner diameter and an outer diameter;
   said second end having means for sealing said end to a tubular member, said means for sealing including at least one integral annular sealing band; and
   said swivel track including an annular collar circumscribing said body, being integrally secured to said body by an annular shoulder, and having an annular sealing rib projecting inwardly from an inner surface of said collar.

2. The swivel member as defined in claim 1 wherein said inner diameter of said first open end is dimensioned to matingly engage an endotracheal connector.

3. The swivel member as defined in claim 2 wherein said inner diameter is on the order of 12 to 17 mm.

4. The swivel member as defined in claim 1 wherein said outer diameter of said first open end is dimensioned to matingly engage a respiratory face mask.

5. The swivel member as defined in claim 4 wherein said outer diameter of said first open end is on the order of 19 to 25 mm.

6. The swivel member as defined in claim 1 wherein said first open end has a dual wall construction including an outer wall dimensioned for mating engagement with a face mask, an inner wall dimensioned to matingly engage an endotracheal connector, and a gap defined between said outer and inner walls, said outer wall being of greater diameter than said inner wall.

7. The swivel member as defined in claim 1 wherein said means for sealing said second end portion includes three integral annular sealing bands located in spaced relationship near said central portion.

8. The swivel member as defined in claim 1 wherein said annular sealing rib is centrally located on an underside of said annular collar.

9. A respiratory connector having swivelling ends, comprising:
   a tubular body having a first end with a male formation and a second end with a female formation;
   a first tubular swivel member disposed so as to matingly engage said male formation;
   a second tubular swivel member disposed so as to matingly engage said female formation;
   said first and second tubular swivel members being substantially identical in construction, each of said first and second tubular swivel members including a tubular body having a first open end, a second open end and a central portion, said first open end having an inner diameter and an outer diameter, and said second end having means for sealing said second end to a tubular member; and
   said central portion having an annular collar secured to said central portion by an annular shoulder in spaced, concentric relation, said annular collar having a depending annular sealing rib for sealingly and swivellingly engaging the tubular member.

10. The connector as defined in claim 9 wherein said connector body forms a 90 degree angle.

11. The connector as defined in claim 9 wherein said second connector body end is provided with an annular groove adjacent an outer edge thereof, and an annular ring having a shoulder, said groove being disposed between said outer edge and said ring.

12. The connector as defined in claim 9 wherein said first open end has a dual wall construction.

13. The connector as defined in claim 9 wherein said means for sealing said second open end is at least one annular sealing ring.

14. The connector as defined in claim 9 further including at least one access port.

15. The connector as defined in claim 14 including a plurality of said access ports wherein at least one of said access ports is configured as a luer fitting.

16. The connector as defined in claim 14 wherein each of said access ports is provided with a tethered cap.

17. A combination respiratory 'Y'-piece and swivelling elbow connector, comprising:
   a tubular 'Y'-piece having an inhalation tube socket, an exhalation tube socket and a connector tube, said connector tube having a sealing formation;
   a first swivel member having a first open end, a second open end, and a central portion, said second open end configured for insertion into said connector tube, and said central portion having a swivel track defined by an annular collar circumscribing said central portion and being held in spaced relation thereto by an integral shoulder, said collar having a seal formation configured for sealing, swivelling engagement with said connector tube sealing formation;
   a tubular elbow connector having a male end and a female end, said male end configured for insertion into the first open end of said first swivel member, said female end having a sealing formation; and
   a second swivel member having a first open end, a second open end, and a central portion, said second open end configured for insertion into said female end of said elbow connector for swivelling engagement therewith.

18. The combination as defined in claim 17 wherein said first and second swivel members are substantially identical.

19. The combination as defined in claim 18 wherein each of said swivel members includes a dual wall construction on said first end, said second end having at least one annular sealing band, and said seal formation on said annular collar being a depending annular sealing rib.

20. The combination as defined in claim 17 wherein an end of said connector tube of said 'Y'-piece and said female end of said elbow connector are each provided with an annular groove adjacent an outer edge thereof, and an annular ring having a shoulder, said groove being disposed between said outer edge and said ring for forming a sealing relationship with said central portion of one of said first and second swivel members, respectively.

* * * * *